United States Patent
Kawamura

(10) Patent No.: US 11,478,209 B2
(45) Date of Patent: Oct. 25, 2022

(54) IMAGE PROCESSING APPARATUS, METHOD, AND PROGRAM

(71) Applicant: FUJIFILM Corporation, Tokyo (JP)

(72) Inventor: Takahiro Kawamura, Kanagawa (JP)

(73) Assignee: FUJIFILM Corporation, Tokyo (JP)

(*) Notice: Subject to any disclaimer, the term of this patent is extended or adjusted under 35 U.S.C. 154(b) by 63 days.

(21) Appl. No.: 17/060,284

(22) Filed: Oct. 1, 2020

(65) Prior Publication Data
US 2021/0100520 A1   Apr. 8, 2021

(30) Foreign Application Priority Data
Oct. 4, 2019   (JP) .............................. JP2019-184032

(51) Int. Cl.
| | | |
|---|---|---|
| *G06K 9/00* | (2022.01) | |
| *A61B 6/00* | (2006.01) | |
| *G06T 7/00* | (2017.01) | |
| *G06T 7/62* | (2017.01) | |

(52) U.S. Cl.
CPC .......... *A61B 6/5217* (2013.01); *A61B 6/4266* (2013.01); *A61B 6/461* (2013.01); *A61B 6/5252* (2013.01); *G06T 7/0014* (2013.01); *G06T 7/62* (2017.01); *G06T 2207/10116* (2013.01); *G06T 2207/30004* (2013.01)

(58) Field of Classification Search
None
See application file for complete search history.

(56) References Cited

U.S. PATENT DOCUMENTS

| | | | |
|---|---|---|---|
| 2004/0101086 A1* | 5/2004 | Sabol | A61B 6/482 378/4 |
| 2008/0232668 A1* | 9/2008 | Kitamura | G06T 7/11 382/132 |
| 2011/0305405 A1 | 12/2011 | Kawamura | |
| 2014/0371570 A1* | 12/2014 | Davis | A61B 6/482 600/407 |
| 2015/0379711 A1 | 12/2015 | Imai | |
| 2017/0360391 A1* | 12/2017 | Kawamura | A61B 6/542 |
| 2018/0263559 A1* | 9/2018 | Kawamura | A61B 5/4872 |
| 2018/0325476 A1* | 11/2018 | Machida | A61B 6/12 |
| 2019/0223788 A1* | 7/2019 | Schultes | A61B 5/0064 |
| 2020/0250824 A1* | 8/2020 | Yi | G01N 23/04 |

FOREIGN PATENT DOCUMENTS

| | | | | |
|---|---|---|---|---|
| EP | 1044649 A1 | * 10/2000 | | A61B 6/032 |
| EP | 2238905 A1 | * 10/2010 | | A61B 5/4312 |
| JP | 2011-255060 A | 12/2011 | | |
| JP | 2014-207958 A | 11/2014 | | |
| JP | 2018-153605 A | 10/2018 | | |
| WO | WO-2016200983 A1 | * 12/2016 | | A61B 6/502 |

* cited by examiner

*Primary Examiner* — Atiba O Fitzpatrick
(74) *Attorney, Agent, or Firm* — Studebaker & Brackett PC

(57) ABSTRACT

An image acquisition unit acquires two radiographic images based on radiations which are transmitted through a subject containing a plurality of compositions and have energy distributions different from each other. A body thickness derivation unit derives, as a first body thickness and a second body thickness, body thicknesses of the subject for pixels of the two radiographic images. A composition ratio derivation unit derives composition ratios of the subject for the pixels of the radiographic images based on the first body thickness and the second body thickness.

12 Claims, 5 Drawing Sheets

IMAGE PROCESSING APPARATUS, METHOD, AND PROGRAM

CROSS-REFERENCE TO RELATED APPLICATIONS

This application claims priority from Japanese Patent Application No. 2019-184032, filed Oct. 4, 2019 the disclosure of which is incorporated herein by reference in their entirety.

BACKGROUND

Technical Field

The present disclosure relates to image processing apparatus, method, and program for deriving a composition ratio of a subject by using a radiographic image.

Related Art

In the related art, various methods for deriving compositions of a human body such as fat and muscle have been proposed. For example, in JP2018-153605A, a method of generating a soft part image indicating a soft part tissue of a subject from a plurality of radiographic images acquired by radiations which are transmitted through the subject and have energy distributions different from each other, estimating a body thickness distribution of the subject based on an imaging condition in the case of acquiring the soft part image and the radiographic images, calculating an approximate body thickness distribution obtained by approximating the estimated body thickness distribution in a model corresponding to the human body, and calculating a distribution of body fat percentages in the subject based on the approximate body thickness distribution has been proposed. Particularly, in the method described in JP2018-153605A, a distance between a radiation source and a radiation detector (source to image receptor distance (SID)) is used as the imaging condition for estimating the body thickness distribution. [0004] However, the SID in the method described in JP2018-153605A is difficult to be accurately measured, and thus, there is a possibility that the body fat percentage cannot be accurately calculated in the method described in JP2018-153605A. Thus, it is desirable that a fat composition ratio of the subject is accurately obtained.

SUMMARY

The present disclosure has been made in view of the above circumstances, and an object of the present disclosure is to enable a composition ratio in a subject to be accurately derived.

An image processing apparatus according to the present disclosure comprising an image acquisition unit that acquires two radiographic images based on radiations which are transmitted through a subject containing a plurality of compositions and have energy distributions different from each other, a body thickness derivation unit that derives, as a first body thickness and a second body thickness, body thicknesses of the subject for pixels of the two radiographic images, and a composition ratio derivation unit that derives composition ratios of the subject for the pixels of the radiographic images based on the first body thickness and the second body thickness.

An image processing method according to the present disclosure comprises acquiring two radiographic images based on radiations which are transmitted through a subject containing a plurality of compositions and have energy distributions different from each other, deriving, as a first body thickness and a second body thickness, body thicknesses of the subject for pixels of the two radiographic images, and deriving composition ratios of the subject for the pixels of the radiographic images based on the first body thickness and the second body thickness.

An image processing program causing a computer to execute the image processing method according to the present disclosure may be provided.

Another image processing apparatus according to the present disclosure comprises a memory that stores a command to be executed by a computer, and a processor configured to execute the stored command. The processor executes processing of acquiring two radiographic images based on radiations which are transmitted through a subject containing a plurality of compositions and have energy distributions different from each other, deriving, as a first body thickness and a second body thickness, body thicknesses of the subject for pixels of the two radiographic images, and deriving composition ratios of the subject for the pixels of the radiographic images based on the first body thickness and the second body thickness.

According to the present disclosure, composition ratios in a subject can be accurately derived.

DETAILED DESCRIPTION

Figure 1:
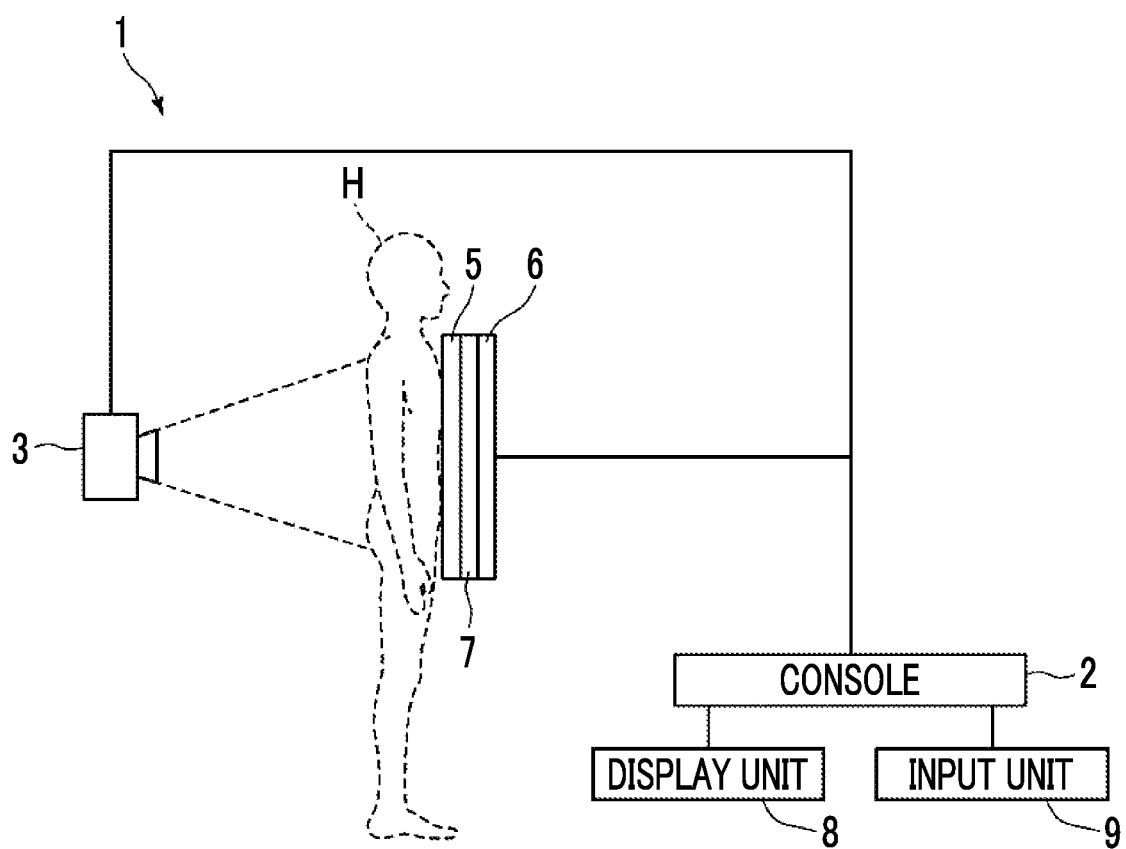
FIG. 1 is a schematic configuration diagram of a radiographic image imaging apparatus to which an image processing apparatus according to an embodiment of the present disclosure is applied.

Hereinafter, embodiments of the present disclosure will be described with reference to the drawings. FIG. 1 is a schematic block diagram showing a configuration of a radiographic image imaging system to which an image processing apparatus according to a first embodiment of the present disclosure is applied. As shown in FIG. 1, the radiographic image imaging system according to the first embodiment can image two radiographic images having different energy distributions and can perform energy subtraction processing by using the two radiographic images, and includes an imaging apparatus 1 and a console 2 incorporating the image processing apparatus according to the present embodiment.

The imaging apparatus 1 is an imaging apparatus that performs energy subtraction using a so-called one-shot method of irradiating a first radiation detector 5 and a second radiation detector 6 with radiations such as X-rays which is emitted from a radiation source 3 and is transmitted through a subject H while changing energies. In the case of performing the imaging, the first radiation detector 5, a radiation energy conversion filter 7 made of a copper plate, and the second radiation detector 6 are arranged in this order from a side closer to the radiation source 3 as shown in FIG. 1, and the radiation source 3 is driven. The first and second radiation detectors 5 and 6 and the radiation energy conversion filter 7 are closely attached to each other.

Accordingly, the first radiation detector 5 acquires a first radiographic image G1 of the subject H by a low energy radiation including so-called soft rays. The second radiation detector 6 acquires a second radiographic image G2 of the subject H by a high energy radiation from which the soft rays are removed. The first and second radiographic images are input to the console 2. In the present embodiment, in the case of imaging the subject H, a scattered radiation removal grid that removes scattered radiation components of the radiations transmitted through the subject H is not used. Thus, the first radiographic image G1 and the second radiographic image G2 include primary radiation components and scattered radiation components of the radiations transmitted through the subject H.

The energy subtraction processing is processing of generating an image from which different tissues (for example, a soft part and a bone part) within the subject are extracted by using two radiographic images obtained by irradiating the subject with two types of radiations having different energy distributions by utilizing the fact that the amount of attenuation of the transmitted radiations varies depending on substances constituting the subject. The image imaging apparatus 1 in the radiographic image imaging system according to the present embodiment can perform the energy subtraction processing. However, since the present embodiment derives composition ratios of the subject, the detailed description of the energy subtraction processing will be omitted.

The first and second radiation detectors 5 and 6 can repeatedly record and read out the radiographic images. So-called direct type radiation detectors that generate charges by directly receiving radiations may be used, or so-called indirect type radiation detectors that convert radiations into visible light and convert the visible light into charge signals may be used. Although it is desirable that a so-called thin film transistor (TFT) read-out method of reading out radiographic image signals by turning on and off a TFT switch or a so-called optical read-out method of reading out the radiographic image signals by irradiation of read-out light are used as a method of reading out the radiographic image signals, the present disclosure is not limited thereto, and other methods may be used.

A display unit 8 and an input unit 9 are connected to the console 2. The display unit 8 is a cathode ray tube (CRT), a liquid crystal display, or the like, and assists various inputs necessary for the radiographic images acquired by imaging and processing performed in the console 2.

The input unit 9 is a keyboard, a mouse, or an input device of a touch panel type, and receives an instruction to operate the imaging apparatus 1 from an operator. An instruction to input various kinds of information such as imaging conditions necessary to perform imaging and an instruction to correct information are also received. In the present embodiment, the units of the imaging apparatus 1 operate according to information input by the operator from the input unit 9.

An image processing program according to the first embodiment is installed on the console 2. The console 2 corresponds to the image processing apparatus according to the present embodiment. In the present embodiment, the console 2 may be a workstation or a personal computer directly operated by the operator, or may be a server computer connected to the workstation and the personal computer via a network. The image processing program is stored in a storage device of the server computer connected to the network or a network storage in a state of being accessible from the outside, and is downloaded and installed in the computer according to a request. Alternatively, the image processing program is distributed while being recorded in a recording medium such as a Digital Versatile Disc (DVD) or a compact disc read only memory (CD-ROM), and is installed on the computer from the recording medium.

Figure 2:
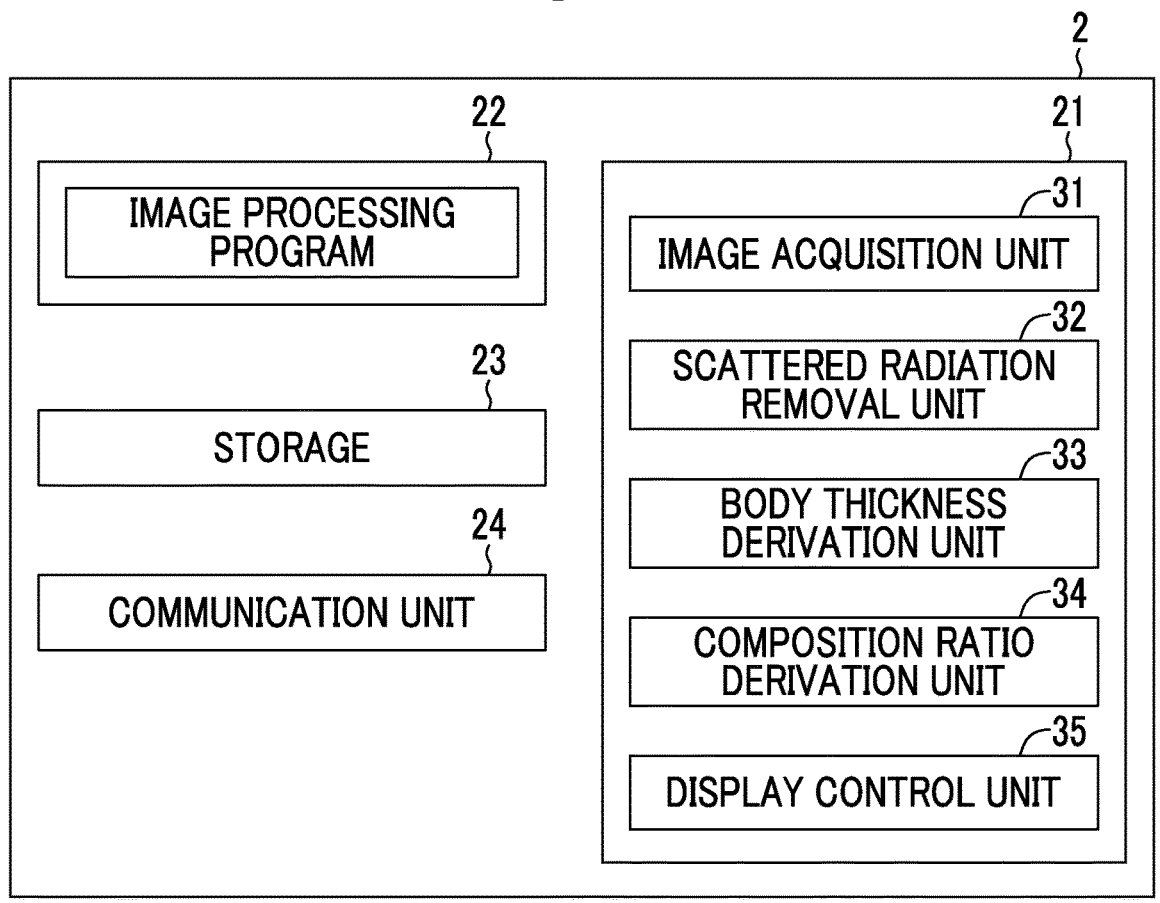
FIG. 2 is a diagram showing a schematic configuration of the image processing apparatus according to the present embodiment.

FIG. 2 is a diagram showing a schematic configuration of the image processing apparatus according to the first embodiment which is realized by installing the image processing program on the computer constituting the console 2. As shown in FIG. 2, the image processing apparatus includes a central processing unit (CPU) 21, a memory 22, a storage 23, and a communication unit 24 as a standard computer configuration.

The storage 23 is a storage device such as a hard disk drive or a solid state drive (SSD), and stores various kinds of information including programs for driving the units of the imaging apparatus 1 and the image processing program. The radiographic images acquired by imaging are also stored.

The communication unit 24 is a network interface that controls transmission of various kinds of information via a network (not shown).

The memory 22 temporarily stores the image processing program and the like stored in the storage 23 in order to cause the CPU 21 to execute various kinds of processing. The image processing program defines, as processing to be executed by the CPU 21, image acquisition processing of acquiring the first and second radiographic images G1 and G2 having energy distributions different from each other by causing the imaging apparatus 1 to perform imaging, scattered radiation removal processing of removing the scattered radiation components included in the first and second radiographic images G1 and G2, body thickness deriving processing of deriving, as a first body thickness and a second body thickness, body thicknesses of the subject H for the pixels of the first and second radiographic images G1 and G2, composition ratio derivation processing of deriving composition ratios of the subject H for the pixels of the radiographic images based on the first body thickness and the second body thickness, and display control processing of displaying a distribution of the composition ratios.

The CPU 21 executes these pieces of processing according to the image processing program, and thus, the console 2 functions as an image acquisition unit 31, a scattered radiation removal unit 32, a body thickness derivation unit 33, a composition ratio derivation unit 34, and a display control unit 35. In the present embodiment, a fat composition ratio is derived as the composition ratio. Thus, the subject H includes the bone part, but it is assumed that the first and second radiographic images G1 and G2 do not include the bone part but only a soft part for the sake of convenience in description.

The image acquisition unit 31 irradiates the subject H with the radiations by driving the radiation source 3, detects the radiations transmitted through the subject H by the first and second radiation detectors 5 and 6, and acquires the first and second radiographic images G1 and G2. At this time, imaging conditions such as an imaging dose, an energy distribution, and a tube voltage are set. The imaging conditions may be set by inputs of the operator from the input unit 9. The set imaging conditions are stored in the storage 23. The first and second radiographic images G1 and G2 may be acquired by a program different from the image processing program and stored in the storage 23. In this case, the image acquisition unit 31 reads out the first and second radiographic images G1 and G2 stored in the storage 23 from the storage 23 in order to perform processing. In the present embodiment, it is assumed that a range from the chest to the abdomen of the subject H is captured and the first and second radiographic images G1 and G2 for the range from the chest to the abdomen are acquired.

The scattered radiation removal unit 32 removes the scattered radiation components which are included in the first and second radiographic images G1 and G2 and are generated by the radiations scattered in the subject H. For example, any method described in JP2014-207958A can be used as a method of removing the scattered radiation components. The method described in JP2014-207958A is a method of performing the scattered radiation removal processing by acquiring characteristics of a grid assumed to be used for removing the scattered radiations in the case of imaging the radiographic images, deriving the scattered radiation components included in the radiographic images based on this characteristics, and using the derived scattered radiation components.

The body thickness derivation unit 33 derives, as the first body thickness and the second body thickness, the body thicknesses of the subject H for the pixels of the first and second radiographic images G1 and G2 from which the scattered radiation components are removed. Specifically, the body thickness derivation unit 33 derives a first body thickness t1 of the subject H by assuming that a brightness distribution of the first radiographic image G1 matches the distribution of the body thickness of the subject H and converting pixel values of the first radiographic image G1 into a thickness by using an attenuation coefficient in the muscle of the subject H. The body thickness derivation unit 33 derives a second body thickness t2 of the subject H by assuming that a brightness distribution of the second radiographic image G2 matches the distribution of the body thickness of the subject H and converting pixel values of the second radiographic image G2 into a thickness by using an attenuation coefficient in the muscle of the subject H.

Here, there are characteristics that the radiations emitted from the radiation source 3 have the energy distributions, the attenuation coefficient of the radiation in the subject H also has a dependency on the energy of the radiation, and the attenuation coefficient becomes smaller as an energy component becomes higher. Thus, a phenomenon called beam hardening in which the radiation relatively loses a large amount of low energy components in the process of transmitting through the substances and a proportion of high energy components increases occurs. Since a degree of beam hardening depends on a fat thickness tf and a muscle thickness tm in the subject H, a fat attenuation coefficient $\mu f$ and a muscle attenuation coefficient $\mu m$ can be defined as $\mu f(tf, tm)$ and $\mu m(tf, tm)$ by non-linear functions of the fat thickness tf and the muscle thickness tm.

As in the present embodiment, the first and second radiographic images G1 and G2 acquired by the radiations having two different energy distributions correspond to a low energy image and a high energy image, respectively. Thus, in the present embodiment, the fat attenuation coefficient and the muscle attenuation coefficient for the first radiographic image G1 which is the low energy image can be represented by $\mu lf(tf, tm)$ and $\mu lm(tf, tm)$, respectively. The fat attenuation coefficient and the muscle attenuation coefficient for the second radiographic image G2 which is the high energy image can be represented by $\mu hf(tf, tm)$ and $\mu hm(tf, tm)$, respectively.

A pixel value G1(x, y) of each pixel of the first radiographic image G1 which is the low energy image and a pixel value G2(x, y) of each pixel of the second radiographic image G2 which is the high energy image are represented by the following Equations (1) and (2) by using a fat thickness tf(x, y), a muscle thickness tm(x, y), and attenuation coefficients $\mu lf(x, y)$, $\mu hf(x, y)$, $\mu lm(x, y)$, and $\mu hm(x, y)$ at the corresponding pixel position. In the Equations (1) and (2), the description of (x, y) is omitted.

$$G1 = \mu lf \times tf + \mu lm \times tm \qquad (1)$$

$$G2 = \mu hf \times tf + \rho hm \times tm \qquad (2)$$

As described above, in the present embodiment, in the case of deriving the first body thickness t1 and the second body thickness t2, the pixel values of the first radiographic image G1 and the second radiographic image G2 are converted into the thicknesses by using the muscle attenuation coefficient in the subject H. Thus, in the first embodiment, the body thickness derivation unit 33 derives the first body thickness t1 and the second body thickness t2 by the following Equations (3) and (4).

$$t1 = G1/\mu lm \qquad (3)$$

$$t2 = G2/\mu hm \qquad (4)$$

Figure 3:
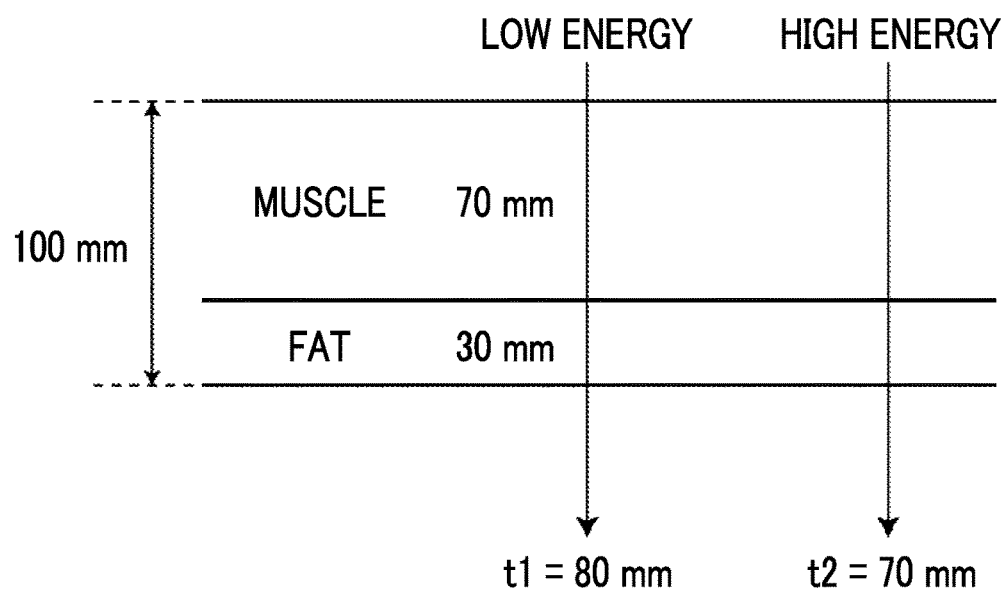
FIG. 3 is a diagram for describing a difference between body thicknesses derived by a low energy image and a high energy image.

In a case where the subject H includes only the muscles at the pixel positions from which the first and second body thicknesses t1 and t2 are derived, the first body thickness t1 and the second body thickness t2 match each other. However, both the muscle and the fat are included in the actual subject H at the same pixel position of the first and second radiographic images G1 and G2. Thus, the first and second body thicknesses t1 and t2 derived from Equations (3) and (4) do not match the actual body thickness of the subject H. Of the first body thickness t1 derived from the first radiographic image G1 which is the low energy image and the second body thickness t2 derived from the second radiographic image G2 which is the high energy image, the first body thickness t1 has a value larger than the second body thickness t2. For example, as shown in FIG. 3, it is assumed that the actual body thickness is 100 mm and the fat and muscle thicknesses are 30 mm and 70 mm, respectively. In this case, the first body thickness t1 derived from the first radiographic image G1 acquired by the low energy radiation is, for example, 80 mm, and the second body thickness t2 derived by the second radiographic image G2 acquired by the high energy radiation is, for example, 70 mm A difference between the first body thickness t1 and the second body thickness t2 becomes larger as the fat composition ratio becomes higher.

Here, the difference between the first body thickness t1 and the second body thickness t2 changes according to the fat and muscle composition ratios in the subject H. Thus, in the present embodiment, a subject model having variously changed fat composition ratios is captured by radiations having different energy distributions, the body thicknesses are derived from two radiographic images acquired by imaging, a difference between the body thicknesses derived from the two radiographic images is associated with the fat composition ratio is created in advance, and the created table is stored in the storage 23.

Figure 4:
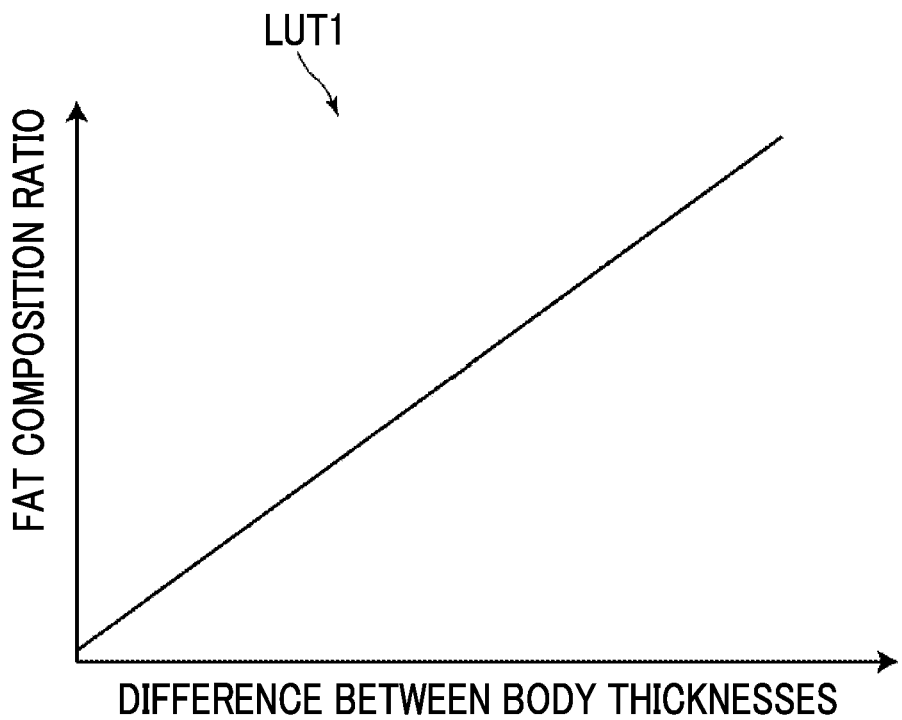
FIG. 4 is a diagram showing a table that defines a relationship between the difference between the body thicknesses and a fat composition ratio.

FIG. 4 is a diagram showing a table in which the difference between the body thicknesses derived from the two radiographic images and the fat composition ratio are associated with each other. As shown in FIG. 4, in a table LUT1, a horizontal axis represents the difference between the body thicknesses derived from the two radiographic images, and a vertical axis represents the fat composition ratio. As shown in FIG. 4, as the difference between the body thicknesses derived from the two radiographic images becomes larger, the fat composition ratio becomes higher. The table in which the difference between the body thicknesses derived from the two radiographic images and the fat composition ratio are associated with each other is prepared for each energy distribution of the radiations used in the case of performing the imaging, and is stored in the storage 23.

The composition ratio derivation unit 34 derives the difference between the first body thickness t1 and the second body thickness t2 derived by the body thickness derivation unit 33, and derives the fat composition ratio while referring to the LUT1 stored in the storage 23. The muscle composition ratio can be derived by subtracting the derived fat composition ratio from 100%.

Figure 5:
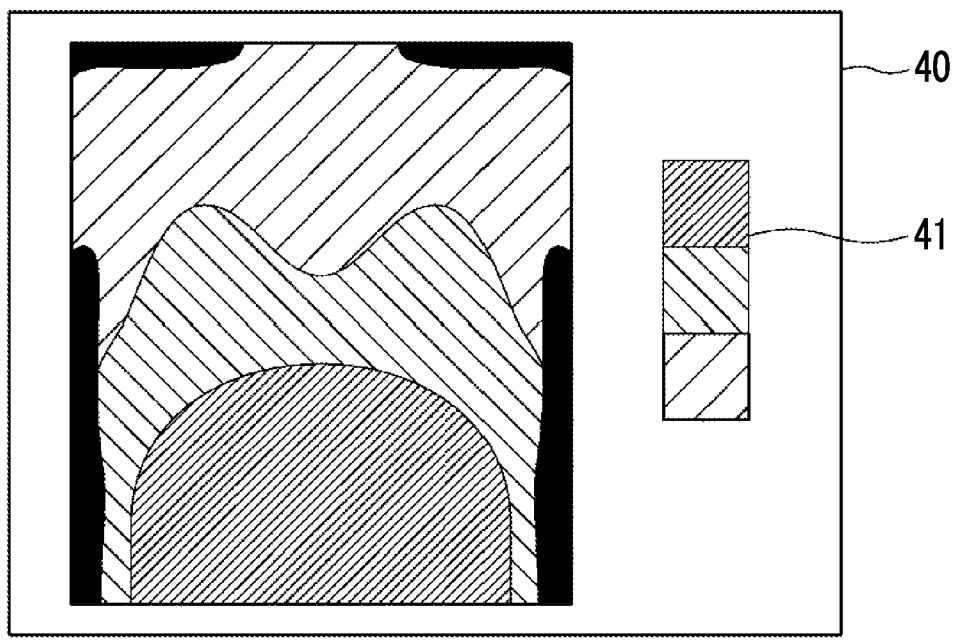
FIG. 5 is a diagram showing a display screen of a body fat percentage.

The display control unit 35 displays the fat composition distribution on the display unit 8 based on the fat composition ratios for the pixels of the first and second radiographic images G1 and G2 derived by the composition ratio derivation unit 34. FIG. 5 is a diagram showing a display screen of the fat composition distribution displayed on the display unit 8. As shown in FIG. 5, the fat composition distribution is displayed as a body fat percentage distribution so as to be superimposed on the first radiographic image G1 on the display screen 40. The body fat percentage distribution may be superimposed on the second radiographic image G2. In FIG. 5, the body fat percentage distribution is displayed by performing color coding in three different colors. In FIG. 5, the color coding is represented by a density difference, and as a density becomes higher, a body fat percentage becomes higher. A reference 41 indicating a relationship between the density and the body fat percentage is displayed on the display unit 8. The body fat percentage distribution can be easily recognized while referring to the reference 41.

Figure 6:
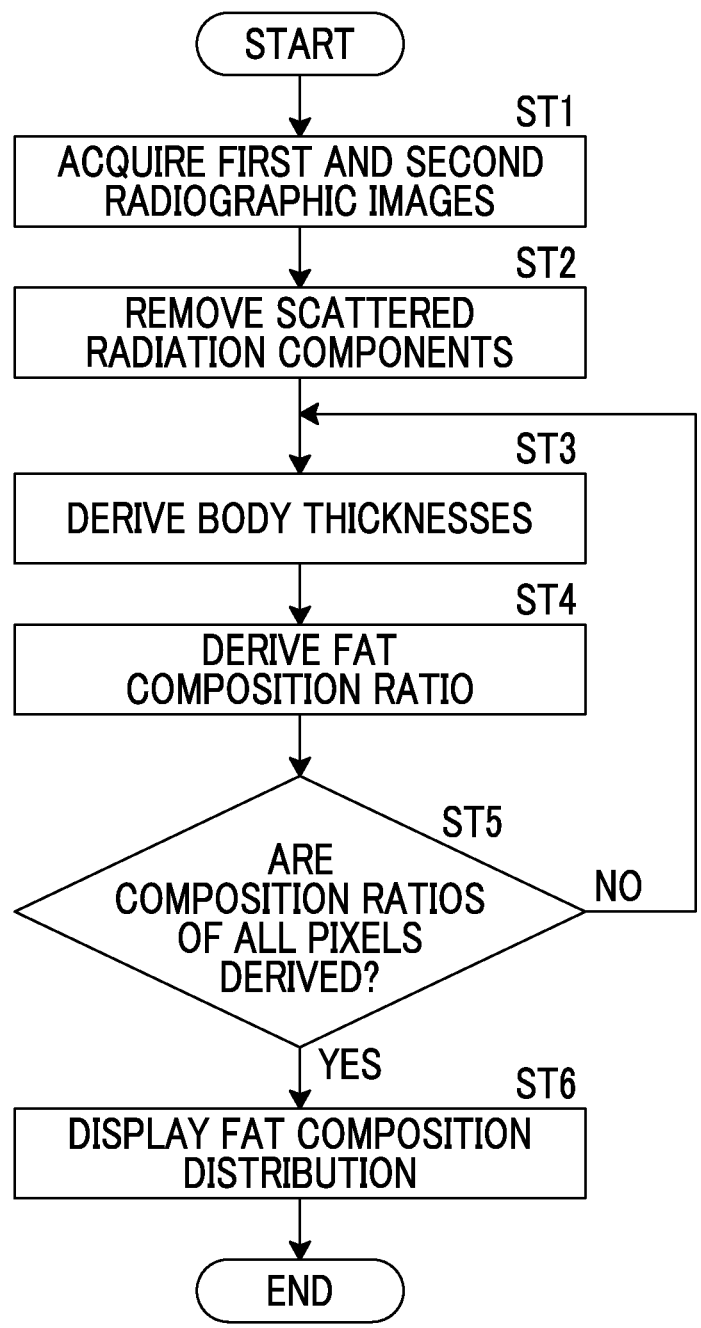
FIG. 6 is a flowchart showing processing performed in a first embodiment.

Next, processing performed in the first embodiment will be described. FIG. 6 is a flowchart showing the processing performed in the first embodiment. It is assumed that the first and second radiographic images G1 and G2 are acquired by imaging and are stored in the storage 23. In a case where an instruction to start the processing is input from the input unit 9, the image acquisition unit 31 acquires the first and second radiographic images G1 and G2 from the storage 23 (step ST1). Subsequently, the scattered radiation removal unit 32 removes the scattered radiation components from the first and second radiographic images G1 and G2 (step ST2). The body thickness derivation unit 33 derives, as the first body thickness t1 and the second body thickness t2, the body thicknesses of the subject H for the pixels of the first and second radiographic images G1 and G2 from which the scattered radiation components are removed (step ST3).

Subsequently, the composition ratio derivation unit 34 derives the difference between the first body thickness t1 and the second body thickness t2 derived by the body thickness derivation unit 33, and derives the fat composition ratio while referring to the LUT1 stored in the storage 23 (step ST4). The composition ratio derivation unit 34 determines whether or not the composition ratios of all the pixels are derived (step ST5), and in a case where the determination of step ST5 is negative, the processing returns to step ST3. Accordingly, the processing of steps ST3 to ST5 is repeated. In a case where the determination of step ST5 is positive, the display control unit 35 displays the fat composition distribution based on the fat composition ratio derived by the composition ratio derivation unit 34 on the display unit 8 (step ST6), and the processing ends.

As described above, in the first embodiment, the body thicknesses of the subject H are derived as the first body thickness t1 and the second body thickness t2 for the pixels of the first and second radiographic images G1 and G2, and the composition ratios of the subject H are derived based on the difference between the first body thickness t1 and the second body thickness t2. Thus, an accurate SID becomes unnecessary as described in JP2018-153605A. Therefore, according to the present embodiment, the composition ratio in the subject can be accurately derived.

Although it has been described in the first embodiment that the body thickness derivation unit 33 derives the first and second body thicknesses t1 and t2 by converting the pixel values of the first and second radiographic images G1 and G2 into the thicknesses by using the muscle attenuation coefficient, the present disclosure is not limited thereto. The first and second body thicknesses t1 and t2 may be derived by converting the pixel values of the first and second radiographic images G1 and G2 into thicknesses by using the fat attenuation coefficient. In this case, the table in which the difference between the body thicknesses derived from the two radiographic images and the muscle composition ratio are associated with each other is created in advance and is stored in the storage 23. The composition ratio derivation unit 34 may derive the muscle composition ratio while referring to the table in which the difference between the body thicknesses derived from the two radiographic images and the muscle composition ratio are associated with each other. In this case, the fat composition ratio can be derived by subtracting the derived muscle composition ratio from 100%.

Next, a second embodiment of the present disclosure will be described. An image processing apparatus according to the second embodiment has the same configuration as the image processing apparatus according to the first embodiment of the present disclosure shown in FIG. 2, and has a difference in only processing to be performed. Thus, the detailed description of the apparatus is omitted herein. The image processing apparatus according to the second embodiment is different from the first embodiment in that the body thickness derivation unit 33 derives the first body thickness t1 and the second body thickness t2 based on the attenuation coefficients of the radiations for different energy distributions for a plurality of compositions, and the composition ratio derivation unit 34 causes the body thickness derivation unit 33 to derive the first body thickness t1 and the second body thickness t2 while changing the thickness of the composition and the attenuation coefficient of each composition and derives the composition ratio based on the thickness of the composition at which the difference between the first body thickness t1 and the second body thickness t2 is equal to or less than a predetermined threshold value Th1.

Here, the first body thickness t1 is the sum of the fat thickness tf and the muscle thickness tm, that is, t1=tf+tm. Since tm=t1−tf, the above Equation (1) can be transformed into the following Equation (5).

$$G1 = \mu lf \times tf + \mu lm \times (t1 - tf) \quad (5)$$

In a case where Equation (5) is solved for t1, the following Equation (5) is obtained.

$$t1 = \{G1 + (\mu lm - \mu lf) \times tf\}/\mu lm \quad (6)$$

Since the second body thickness t2=tf+tm, in a case where Equation (2) is transformed in the same manner as Equation (5) and is solved for t2, the following Equation (7) is obtained.

$$t2=\{G2+(\mu hm-\mu hf)\times tf\}/\mu hm \quad (7)$$

The fat composition ratio can be derived by deriving the fat thickness tf such that the difference between t1 and t2 becomes small and preferably t1=t2. However, since the attenuation coefficients μlf, μhf, μlm, and μhm are the non-linear functions of the fat thickness tf and the muscle thickness tm, the fat thicknesses tf cannot be algebraically derived from Equations (6) and (7). Thus, in the second embodiment, the composition ratio derivation unit 34 causes the body thickness derivation unit 33 to derive the first body thickness t1 and the second body thickness t2 while changing the fat thickness tf and the attenuation coefficients μlf, μhf, μlm, and μhm. The composition ratio derivation unit 34 derives the fat thickness tf at which the difference between the first body thickness t1 and the second body thickness t2 is equal to or less than the predetermined threshold value Th1, that is, |t1−t2|≤Th1, and derives the fat composition ratio based on the fat thickness tf. The threshold value Th1 is preferably as small as possible, and more preferably Th1=0.

Specifically, in a case where tf=0 and t1=t2, all the pixels (x, y) are muscles. In a case where tf=0 and t1≠t2, the composition ratio derivation unit 34 derives the fat thickness tf by searching for the fat thickness tf at which |t1−t2|≤Th1 while changing the fat thickness tf. The composition ratio derivation unit 34 derives the fat composition ratio by dividing the derived fat thickness tf by the first body thickness t1 or the second body thickness t2. The muscle composition ratio can be derived by subtracting the derived fat composition ratio from 100%.

Figure 7:
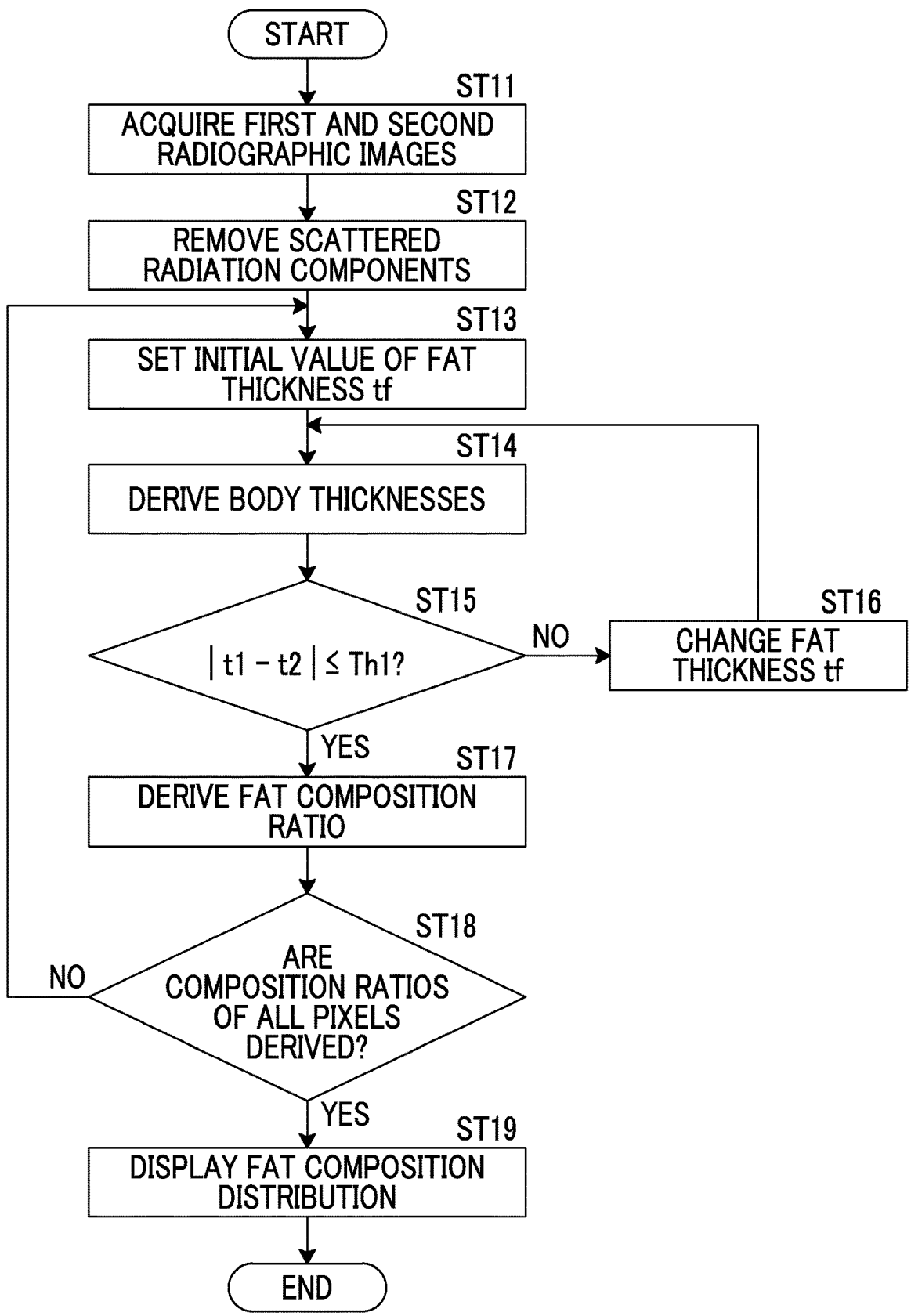
FIG. 7 is a flowchart showing processing performed in a second embodiment.

Next, processing performed in the second embodiment will be described. FIG. 7 is a flowchart showing the processing performed in the second embodiment. It is assumed that the first and second radiographic images G1 and G2 are acquired by imaging and are stored in the storage 23. In a case where an instruction to start the processing is input from the input unit 9, the image acquisition unit 31 acquires the first and second radiographic images G1 and G2 from the storage 23 (step ST11). Subsequently, the scattered radiation removal unit 32 removes the scattered radiation components from the first and second radiographic images G1 and G2 (step ST12). The body thickness derivation unit 33 sets an initial value of the fat thickness tf (step ST13), and derives, as the first body thickness t1 and the second body thickness t2, the body thicknesses of the subject H for the pixels of the first and second radiographic images G1 and G2 from which the scattered radiation components are removed (step ST14). The initial value of the fat thickness tf may be set by the composition ratio derivation unit 34.

Subsequently, the composition ratio derivation unit 34 determines whether or not |t1−t2|≤Th1 (step ST15), and in a case where the determination of step ST15 is negative, the fat thickness tf is changed (step ST16), and the processing returns to step ST14. Accordingly, the processing of steps ST14 to ST16 is repeated. In a case where the determination of step ST15 is positive, the composition ratio derivation unit 34 derives the fat composition ratio based on the fat thickness tf in a case where the determination of step ST15 is positive (step ST17). The composition ratio derivation unit 34 determines whether or not the composition ratios of all the pixels are derived (step ST18), and in a case where the determination of step ST18 is negative, the processing returns to step ST13. Accordingly, the processing of steps ST13 to ST18 is repeated. In a case where the determination of step ST18 is positive, the display control unit 35 displays the fat composition distribution based on the fat composition ratio derived by the composition ratio derivation unit 34 on the display unit 8 (step ST19), and the processing ends.

As stated above, in the second embodiment, since the accurate SID becomes unnecessary as described in JP2018-153605A, the composition ratio in the subject can also be accurately derived.

Although it has been described in the second embodiment that the fat composition ratio is derived based on the fat thickness tf, the muscle composition ratio may be derived based on the muscle thickness tm. In this case, in a case where tf=t1−tm and t1 is derived based on Equation (1), the following Equation (8) is obtained. In a case where Equation (2) is solved for t2, the following Equation (9) is obtained.

$$t1=\{G1+(\mu lf-\mu lm)\times tm\}/\mu lf \quad (8)$$

$$t2=\{G2+(\mu hf-\mu hm)\times tm\}/\mu hf \quad (9)$$

In this case, the composition ratio derivation unit 34 derives the muscle thickness tm by searching for tm at which the difference between the first body thickness t1 and the second body thickness t2 is equal to or less than a predetermined threshold value Th2, that is, |t1−t2|≤Th2, and derives the muscle composition ratio by dividing the derived muscle thickness tm by the first body thickness t1 or the second body thickness t2.

Although it has been described in the above-described embodiments that the scattered radiation removal unit 32 removes the scattered radiation components from the first and second radiographic images G1 and G2, the present disclosure is not limited thereto. For example, in a case where the scattered radiation removal grid is used in the case of performing the imaging, the processing of deriving the composition ratio may be performed without removing the scattered radiation components from the first and second radiographic images G1 and G2. In this case, the scattered radiation removal unit 32 is not necessary for the image processing apparatus of the present embodiment.

Although it has been described in the above-described embodiments that the first and second radiographic images G1 and G2 are acquired by the one-shot method, the first and second radiographic images G1 and G2 may be acquired by a so-called two-shot method of performing imaging twice by using only one radiation detector. In the case of the two-shot method, positions of the subject H included in the first radiographic image G1 and the second radiographic image G2 may shift due to a body movement of the subject H. Thus, it is preferable that the processing of the present embodiment is performed after the positions of the subject in the first radiographic image G1 and the second radiographic image G2 are aligned. For example, the method described in JP2011-255060A can be used as the aligning processing. The method described in JP2011-255060A discloses that a plurality of first bandwidth images and a plurality of second bandwidth images indicating structures having different frequency bandwidths for each of the first and second radiographic images G1 and G2 are generated, the positional shift amount between the corresponding positions in the first bandwidth image and the second bandwidth image of the corresponding frequency bandwidth is acquired, and the positions of the first radiographic image G1 and the second radiographic image G2 are aligned based on the positional shift amount.

Although it has been described in the above-described embodiments that the processing of deriving the composition ratio is performed by using the radiographic images acquired in the system that images the radiographic images G1 and G2 of the subject H by using the first and second radiation detectors 5 and 6, the present disclosure can be applied to a case where the first and second radiographic images G1 and G2 are acquired by using accumulative phosphor sheets as detection units. In this case, the first and second radiographic images G1 and G2 may be acquired by irradiating two overlapped accumulative phosphor sheets with the radiation transmitted through the subject H, accumulating and recording radiographic image information of the subject H in each accumulative phosphor sheet, and photoelectrically reading the radiographic image information from each accumulative phosphor sheet. The two-shot method may also be used in a case where the first and second radiographic images G1 and G2 are acquired by using the accumulative phosphor sheets.

The radiations in each of the above-described embodiments are not particularly limited, and α-rays or γ-rays can be applied in addition to the X-rays.

In each of the above-described embodiments, the following various processors can be used as a hardware structure of processing units that execute various kinds of processing such as the image acquisition unit 31, the scattered radiation removal unit 32, the body thickness derivation unit 33, the composition ratio derivation unit 34, and the display control unit 35 of the console 2 which is the image processing apparatus. As described above, in addition to the CPU which is a general-purpose processor that functions various processing units by executing software (programs), the various processors include a programmable logic device (PLD) which is a processor capable of changing a circuit configuration after a field programmable gate array (FPGA) is manufactured and a dedicated electrical circuit which is a processor having a circuit configuration specifically designed in order to execute specific processing such as an application specific integrated circuit (ASIC).

One processing unit may be constituted by one of these various processors, or may be constituted by a combination of two or more processors of the same type or different types (for example, a combination of a plurality of FPGAs or a combination of a CPU and an FPGA). The plurality of processing units may be constituted by one processor.

As an example in which the plurality of processing units is constituted by one processor, firstly, one processor is constituted by a combination of one or more CPUs and software as represented by computers such as clients and servers, and this processor functions as the plurality of processing units. Secondly, a processor that realizes the functions of the entire system including the plurality of processing units by one integrated circuit (IC) chip is used as represented by a system on chip (SoC). As described above, the various processing units are constituted by using one or more of the various processors as the hardware structure.

More specifically, an electric circuitry in which circuit elements such as semiconductor elements are combined can be used as the hardware structure of these various processors.

In the image processing apparatus according to the present disclosure, the composition ratio derivation unit may derive the composition ratios based on a difference between the first body thickness and the second body thickness.

In the image processing apparatus according to the present disclosure, the body thickness derivation unit may derive the first body thickness and the second body thickness based on attenuation coefficients of the radiations having the different energy distributions for the plurality of compositions, and the composition ratio derivation unit may cause the body thickness derivation unit to derive the first body thickness and the second body thickness while changing thicknesses of the compositions and attenuation coefficients of the compositions, and may derive the composition ratios based on the thicknesses of the compositions at which a difference between the first body thickness and the second body thickness is equal to or less than a predetermined threshold value.

The image processing apparatus according to the present disclosure may further comprise a scattered radiation removal unit that removes scattered radiation components included in the two radiographic images.

In the image processing apparatus according to the present disclosure, the two radiographic images may be acquired by two detection units overlapped with each other by simultaneously irradiating the two detection units with the radiations transmitted through the subject.

The image processing apparatus according to the present disclosure may further comprise a display control unit that displays a distribution of the composition ratios in superimposition with any of the two radiographic images on a display unit.

In the image processing apparatus according to the present disclosure, the plurality of compositions may be muscle and fat.

What is claimed is:

1. An image processing apparatus comprising a processor that is configured to:
   acquire a first radiographic image and a second radiographic image based on radiations which are transmitted through a subject containing a plurality of compositions and have energy distributions different from each other;
   derive, as a first body thickness, a body thickness of the subject for pixels of the first radiographic image and derive, as a second body thickness, a body thickness of the subject for pixels of the second radiographic image; and
   derive composition ratios of the subject for the corresponding pixels of the first radiographic image and the second radiographic image based on the first body thickness and the second body thickness, wherein
   the processor derives the composition ratios based on a difference between the first body thickness and the second body thickness.

2. An image processing apparatus comprising a processor that is configured to:
   acquire a first radiographic image and a second radiographic image based on radiations which are transmitted through a subject containing a plurality of compositions and have energy distributions different from each other;
   derive, as a first body thickness, a body thickness of the subject for pixels of the first radiographic image and derive, as a second body thickness, a body thickness of the subject for pixels of the second radiographic image; and
   derive composition ratios of the subject for the corresponding pixels of the first radiographic image and the second radiographic image based on the first body thickness and the second body thickness, wherein
   the processor is further configured to:

derive the first body thickness and the second body thickness based on attenuation coefficients of the radiations having the different energy distributions for the plurality of compositions; and derive the first body thickness and the second body thickness while changing thicknesses of the compositions and attenuation coefficients of the compositions, and derive the composition ratios based on the thicknesses of the compositions at which a difference between the first body thickness and the second body thickness is equal to or less than a predetermined threshold value.

3. The image processing apparatus according to claim 1, wherein the processor is further configured to remove scattered radiation components included in the first radiographic image and the second radiographic image.

4. The image processing apparatus according to claim 2, wherein the processor is further configured to remove scattered radiation components included in the first radiographic image and the second radiographic image.

5. The image processing apparatus according to claim 1, wherein the first radiographic image and the second radiographic image are acquired by two detectors overlapped with each other by simultaneously irradiating the two detectors with the radiations transmitted through the subject.

6. The image processing apparatus according to claim 2, wherein the first radiographic image and the second radiographic image are acquired by two detectors overlapped with each other by simultaneously irradiating the two detectors with the radiations transmitted through the subject.

7. The image processing apparatus according to claim 1, wherein the processor is further configured to display a distribution of the composition ratios in superimposition with any of the first radiographic image and the second radiographic image on a display.

8. The image processing apparatus according to claim 2, wherein the processor is further configured to display a distribution of the composition ratios in superimposition with any of the first radiographic image and the second radiographic image on a display.

9. The image processing apparatus according to claim 1, wherein the plurality of compositions is muscle and fat.

10. The image processing apparatus according to claim 2, wherein the plurality of compositions is muscle and fat.

11. An image processing method comprising:

acquiring a first radiographic image and a second radiographic image based on radiations which are transmitted through a subject containing a plurality of compositions and have energy distributions different from each other;

deriving, as a first body thickness, a body thickness of the subject for pixels of the first radiographic image and deriving, as a second body thickness, a body thickness of the subject for pixels of the second radiographic image; and deriving composition ratios of the subject for the corresponding pixels of the first radiographic and the second radiographic image based on the first body thickness and the second body thickness, wherein the method comprises deriving the composition ratios based on a difference between the first body thickness and the second body thickness.

12. A non-transitory computer-readable storage medium storing an image processing program causing a computer to execute:

acquiring a first radiographic image and a second radiographic image based on radiations which are transmitted through a subject containing a plurality of compositions and have energy distributions different from each other;

deriving, as a first body thickness, a body thickness of the subject for pixels of the first radiographic image and deriving, as a second body thickness, a body thickness of the subject for pixels of the second radiographic image; and deriving composition ratios of the subject for the corresponding pixels of the first radiographic and the second radiographic image based on the first body thickness and the second body thickness, wherein the image processing program causes the computer to execute deriving the composition ratios based on a difference between the first body thickness and the second body thickness.

* * * * *